United States Patent [19]
Gil et al.

[11] Patent Number: 5,665,088
[45] Date of Patent: Sep. 9, 1997

[54] BONE SECTION REATTACHMENT APPARATUS AND METHOD

[75] Inventors: Carlos E. Gil, Bartlett, Tenn.; Michael Ries, Cooperstown, N.Y.; Steven A. Garner, Memphis, Tenn.

[73] Assignee: Smith & Nephew Richards Inc., Memphis, Tenn.

[21] Appl. No.: 660,502

[22] Filed: Jun. 7, 1996

Related U.S. Application Data

[63] Continuation of Ser. No. 132,567, Oct. 6, 1993, abandoned.

[51] Int. Cl.$^6$ ............... A61B 17/80; A61B 17/82
[52] U.S. Cl. ..................... 606/69; 606/74
[58] Field of Search ................ 623/16; 606/69, 606/72, 105, 70, 71, 74, 103

[56] References Cited

U.S. PATENT DOCUMENTS

| | | | |
|---|---|---|---|
| 3,469,573 | 9/1969 | Florio | 606/74 |
| 3,654,668 | 4/1972 | Appleton | |
| 3,745,995 | 7/1973 | Kraus | 623/16 X |
| 3,824,995 | 7/1974 | Getscher et al. | 606/69 |
| 4,153,953 | 5/1979 | Grobbelaar | |
| 4,269,180 | 5/1981 | Dall et al. | |
| 4,473,068 | 9/1984 | Oh | 606/69 |
| 4,530,114 | 7/1985 | Tepic | 623/23 |
| 4,889,110 | 12/1989 | Galline et al. | 606/69 |
| 4,960,420 | 10/1990 | Goble et al. | 606/72 |
| 4,988,351 | 1/1991 | Paulos et al. | |
| 5,002,579 | 3/1991 | Copf et al. | 623/16 X |
| 5,147,360 | 9/1992 | Dubousset | 606/61 |
| 5,190,545 | 3/1993 | Corsi et al. | 606/74 |
| 5,217,497 | 6/1993 | Mehdian | 623/17 |
| 5,324,291 | 6/1994 | Ries et al. | 606/71 |

FOREIGN PATENT DOCUMENTS

| | | |
|---|---|---|
| 0 019 062 | 11/1980 | European Pat. Off. |
| 0 441 668 A1 | 1/1991 | European Pat. Off. |
| 1593644 | 9/1990 | U.S.S.R. ............... 606/72 |
| WO93/03681 | 3/1993 | WIPO |

*Primary Examiner*—David H. Willse
*Attorney, Agent, or Firm*—Pravel, Hewitt, Kimball & Krieger

[57] ABSTRACT

An implant and method for use in reattaching a removed bone section following bone surgery by using a bone engaging clamp adapted to fit over the outer surface of the removed bone section and engage cables to attach the removed bone to the desired location. The bone engaging clamp is adapted to fit over at least a portion of the outer surface of the removed bone section and has an inner surface for engaging the bone section. Further, the bone engaging clamp has at least one through bore for holding a cable; and at least one associated screw for clamping a tensioned cable in a fixed position relative to the bone engaging clamp to hold the removed bone section securely in place at the point of reattachment.

14 Claims, 3 Drawing Sheets

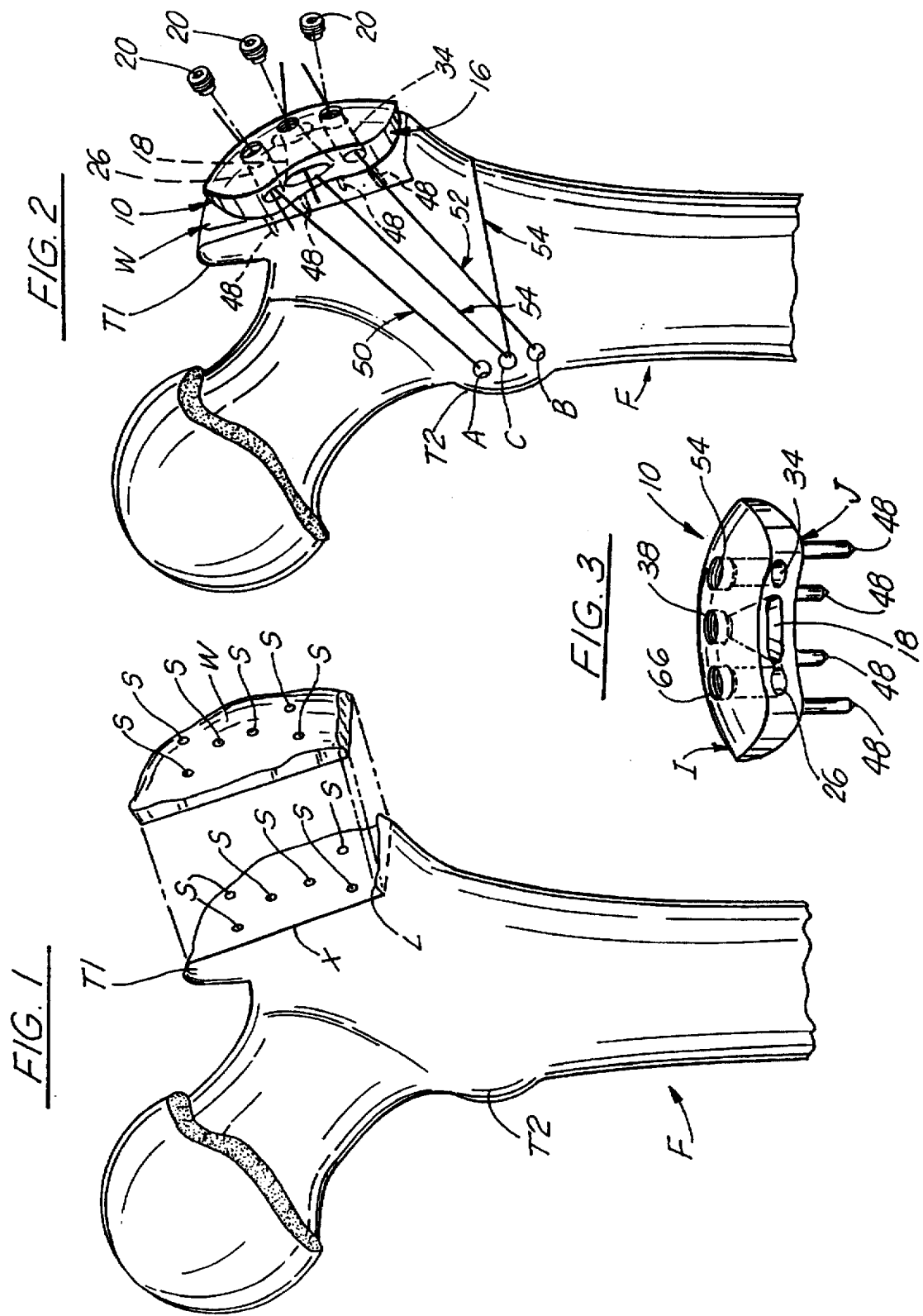

BONE SECTION REATTACHMENT APPARATUS AND METHOD

This is a continuation of application Ser. No. 08/132,567 filed on Oct. 6, 1993, now abandoned.

BACKGROUND OF THE INVENTION

1. Field of the Invention

The invention generally relates to an apparatus and method useful for the reattachment of a bone section removed during surgery and, more particularly, to a clamp and cable system for reattaching the dome portion of the greater trochanter to prevent migration of the removed bone section until it fuses to remaining bone.

2. Description of the Related Art

Hip surgery often requires osteotomy of the dome portion of the greater trochanter to access the hip joint. Following such surgery it is important that removed bone portions that are being replaced are secured in place to promote efficient healing through fusion of the replaced portion with the remainder of the femur.

Many surgeons simply reattach the removed trochanter section after implanting a hip prosthesis by wiring the replaced section to the trochanter. This has proved unsatisfactory because of forces that cause the replaced section to shift or rotate when the patient is walking or rising up from a seat. It is not uncommon for surgical wires to break because of the magnitude of these forces.

A trochanter reattachment system used in the past is known as the Dall-Miles system, described in U.S. Pat. No. 4,269,180. This system utilizes an H-shaped clamp which is held in place on the reattached bone section by teeth that engage the outer surface of the domed segment and teeth that are embedded. Cables are passed through holes in the bridge of the clamp and through holes drilled in the femur. The bridge of the clamp is crimped onto the cables to fix them in position.

The Dall-Miles system has experienced cable failure related problems, which are believed to be caused by sharp bends which the cables are forced to make as they exit the bridge of the clamp. Such cable failures not only result in the clamp loosening but also tissue irritation caused by frayed cable ends.

The Dall-Miles system is not particularly effective in providing rotational and vertical stability for the trochanter segment. Since the attachment cables must pass through the single bridge of the H-shaped clamp, the clamp can rotate about the bridge. Vertical stability is also lacking because the clamp is configured such that the cables must pass through the femur only in a single direction in the vicinity of the lesser trochanter.

U.S. patent application Ser. No. 07/994,320 describes a clamp contoured to fit the outer surface of the domed segment of the greater trochanter. The clamp is formed with angled grooves and insertable cable crimping devices for providing improved rotational and vertical stability, while minimizing the possibility of a failure resulting in loosening of the device or the necessity of its removal. U.S. patent application Ser. No. 07/944,320, filed on Dec. 21, 1992, and entitled Bone Section Reattachment Apparatus and Method, is hereby incorporated by reference.

The reliability with which the greater trochanter can be securely reattached to the femur following osteotomy with a device like the one in Ssr. No. 07/994,320 is improved with the substitution of a mechanical element that provides for positive, adjustable clamping across the entire surface that engages the attachment cables. Therefore, there is a perceived need for the use of a clamp wherein a cable is anchored by the controlled movement of a mechanical device.

SUMMARY OF THE INVENTION

The present invention provides a means to stabilize and support the reattached greater trochanter section until it fuses to the femur. Proper healing is promoted by applying pressure evenly across the osteotomized surface while also providing rotational and vertical stability during the healing process.

In general, the invention implant includes a bone engaging member, preferably of a plate-like construct, that is adapted to fit over at least a portion of the outer surface of a bone section that has been removed. The member has an inner surface for engaging the removed bone section and an outer surface facing away from the bone section. Further, the plate-like member is supplied with at least one means for holding a cable in a fixed position. In order to ensure that the cable is clamped in place, the plate-like member is supplied with means for clamping the cable that is under tension.

In one embodiment, a one-piece, plate-like clamp is contoured to fit on the dome of the greater trochanter. Means, such as spikes, project from the underside of the clamp for providing initial fixation and rotational stability between the clamp, the removed bone section, and the bone. These means also prevent migration while union between removed bone and non-removed bone occurs at the osteotomy site. The clamp is fixed and retained on the osteotomized trochanter section primarily through the use of surgical cables.

The plate-like member is supplied with at least one means for holding a cable in a fixed position relative to the plate-like member. In one embodiment, these means include parallel through bores designed to accommodate cables used to tie the clamp to a femur and extend through the full width of the clamp, from one side to the other. To clamp tensioned cable in the through bores, means operatively associated with the plate-like member's outer surface are provided. These include, in one embodiment, threaded holes formed in the outer surface of the clamp, each hole extending into a through bore. A means for clamping the cable to inner surfaces of the through bores is engaged with the means operatively associated with the outer surface of the plate-like member. These means for clamping to inner surfaces, in one embodiment, includes a screw which is threaded into each of the threaded openings for clamping a cable. After the cables are tensioned, the screws are fully driven into the threaded openings, thereby entering the bores to contact the tensioned cable. By tightening the screws onto the cables in the bores, the cables are clamped or anchored in place. Free cable ends are trimmed to complete the procedure.

In removing a section of the greater trochanter, the bone may be cut along an L-shaped cut line to form a ledge on the lower side of the cut for rotational stability during healing. Additionally, initial fixation and rotational stability between the plate-like member may be provided by forming locating holes the outer surface of the greater trochanter before the bone section is removed. The locating holes are spaced to correspond with means, such as spikes, projecting from on the inner surface of the plate-like member. Once a section of the greater trochanter is removed, the removed bone section and the bone will contain locating holes aligned with the spikes on the plate-like member. The spikes are then inserted into the holes when the plate-like member is positioned on the removed bone section. Once the removed bone section is placed on the bone at the location to which it is to be reattached, a length of cable is wrapped around the bone and through a hole formed in the bone, preferably on the opposite side of the removed bone section. For added support, each of three cables may be wrapped around the bone and passed through one among a plurality of holes formed in the lesser trochanter with one cable wrapping around the lesser trochanter and crossing on the lateral aspect of the femur before going through the plate-like member. The ends of each cable are then passed under cable clamping means associated with the plate-like member and tensioned by pulling on its ends. Finally, the cable clamping means are secured onto the cable ends for holding each cable in tension, and the cable ends are trimmed so that the ends lie within their respective through bores.

BRIEF DESCRIPTION OF THE DRAWINGS

The objects, advantages, and features of the invention will become more apparent when the detailed description of exemplary embodiments is considered in conjunction with the appended drawings, in which:

FIG. 1 is a posterior view of the upper portion of the right femur indicating an osteotomy line for a cut at the base of the greater trochanter and removal a section of the greater trochanter in such a manner that it may be reattached by means of the present invention;

FIG. 2 is a posterior view of the femur of FIG. 1, wherein the greater trochanter section has been removed and prepared for reattachment with a clamp of one embodiment of the present invention;

FIG. 3 is a perspective view of the clamp of one embodiment of the present invention;

DETAILED DESCRIPTION OF THE EXEMPLARY EMBODIMENTS

Referring to FIGS. 1 and 2, reference letter F identifies a femur which has a greater trochanter T1 and a lesser trochanter T2. The femur F has been marked with an osteotomy cut line X in preparation for removal of a fragment or section W of the greater trochanter T1 in conjunction with hip surgery. Following removal of the section W and completion of the hip surgery, the section W is reattached by using a bone engaging member or clamp 10, preferably of a plate-like construct, and surgical cables 50, 52 and 54 as described below.

In preparing the greater trochanter T1, a template (not shown) is overlaid on the outer surface of the greater trochanter T1 and a series of holes S are drilled through the section W to be removed. The spacing of these holes S matches the spacing of a plurality of spikes 48 on the inner surface of clamp 10 and the holes S are sized to cooperate with these spikes 48. The osteotomy cut is then performed along an L-shaped cut line X and the resulting section W of the greater trochanter T1 is removed as shown in FIG. 1. An L-shaped osteotomy cut is preferred, since the resulting ledge L (see FIG. 1) on the lower side of the greater trochanter provides rotational stability during healing. However, the clamp 10 can be used with any other osteotomy cut used to remove the greater trochanter.

Figure 7:
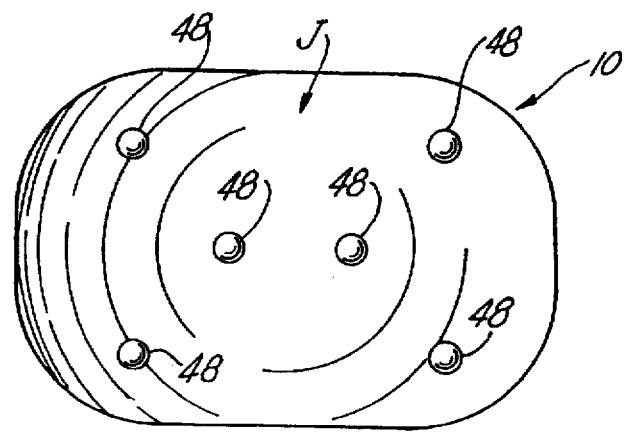
FIG. 7 is a plan view of the underside of the clamp of FIG. 3.

As shown in FIG. 2, upon completion of the surgery during which a prosthetic hip is implanted, the removed section W of the greater trochanter is repositioned on the femur F. A trochanter clamp 10 is positioned on the greater trochanter section W, as shown, so that the spikes 48 (FIG. 7), which project from the underside of the clamp 10, are aligned with the holes S (FIG. 1) to provide greater lateral and rotational stability when the clamp is first installed. The section W with the clamp 10 in place is then repositioned on the superior lateral surface of the greater trochanter T1. After ensuring positioning and alignment of the section W and clamp 10, cable holes about 2.0 mm. in diameter, designated by reference letters A, B and C are drilled through the lesser trochanter T2.

Figure 4:
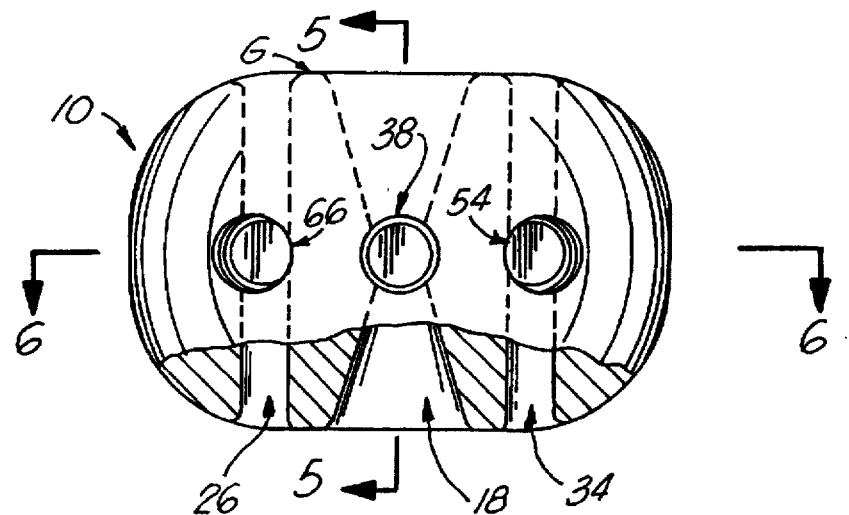
FIG. 4 is a top plan view of the upper surface and a partial section of one embodiment of the clamp of the present invention.
Figure 5:
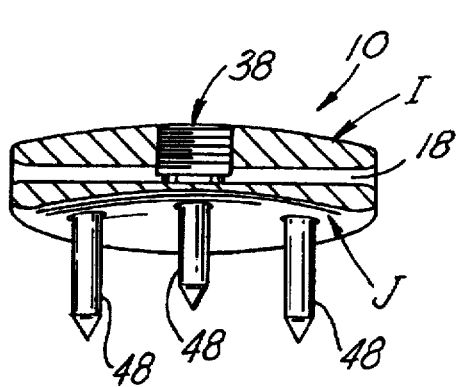
FIG. 5 is a sectional view looking along section line 5—5 of FIG. 4.

The clamp 10, as shown in detail in FIGS. 3–7, has an outer surface I that is generally convex and an inner surface J that faces the removed bone section and that is generally concave. Three parallel through bores 18, 26 and 34 extend laterally through the entire width of the clamp 10 from one side to the other to form openings on opposite sides G and H of the clamp 10 through which cable is threaded. These bores 18, 26 and 34 then provide a means for holding cable in a fixed position relative to the outer surface I of the clamp 10. As shown in FIG. 5, the through bores do not necessarily follow the curved contour of the clamp 10 but the bores may do so, although such may be more difficult to machine.

As shown in FIGS. 3–6, the through bore 18 is formed in the center of the width of the clamp 10. The through bore 18 is formed with openings flaring outwardly from its median point at the center of the clamp 10 to the sides G and H so that the clamp is universal in the sense that it can be used on both the left and right femurs and does not have to be oriented in a particular direction. The through bores 26 and 34 are located on either side of the central through bore 18. Both of the through bores 26 and 34 are formed in a generally tubular shape. (FIG. 4) The size of each through bore is preferably sufficient to accommodate the thickness of two surgical cables as discussed below.

Figure 6:
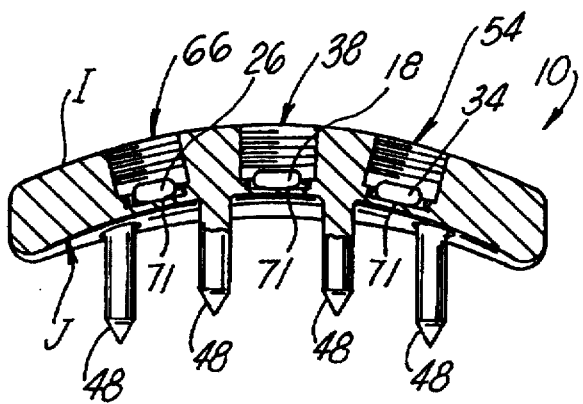
FIG. 6 is a sectional view looking along section line 6—6 of FIG. 4.

It is desirable to affix the clamp 10 and removed bone section W to the greater trochanter with tensioned cable. Thus, the clamp 10 has means operatively associated with its outer surface for cooperating in clamping a tensioned cable. These means cooperate with means for forcing the cable against the inner surfaces of the through bores. Thus, in this example, the means for clamping the cable to the clamp 10 for holding the removed bone section in place, includes: means operatively associated with the outer surface of the clamp 10; means for forcing the cable; and the inner surfaces of the through bores. Referring to FIG. 6, a threaded opening 38 is formed in the center of the upper surface of the clamp 10 substantially perpendicular to and intersecting with the through bore 18. Threaded openings 54 and 66 are similarly formed in the clamp 10 with respect to the through bores 34 and 26. The threaded openings 38, 54 and 66 extend into but not through the through bores 18, 34 and 26, so that the cable can be clamped between the inner surfaces 71 of the through bores and a cooperating means for clamping the cable, such as a bolt or screw, as discussed below.

As shown in FIG. 2, the clamp 10 is installed by passing a length of cable 50 through the hole A and threading the ends through opposite sides of the through bore 26. A second cable 52 is passed through the hole B, with both ends being threaded through opposite sides of the through bore 34. A third cable 54 is centered on the lower side adjacent to the lateral aspect of the femur or adjacent to the lateral cortex and wrapped through hole C and then threaded through bore 18.

The cables 50, 52 and 54 are about 1.6–2.0 mm. in diameter, with the holes A, B and C slightly larger. The cables are preferably formed of braided strands of chrome-cobalt wire. However, cables formed of wires of other biocompatible metals, as well as biocompatible organic polymeric cables or polymer monofilaments, could also be used.

Figure 8:
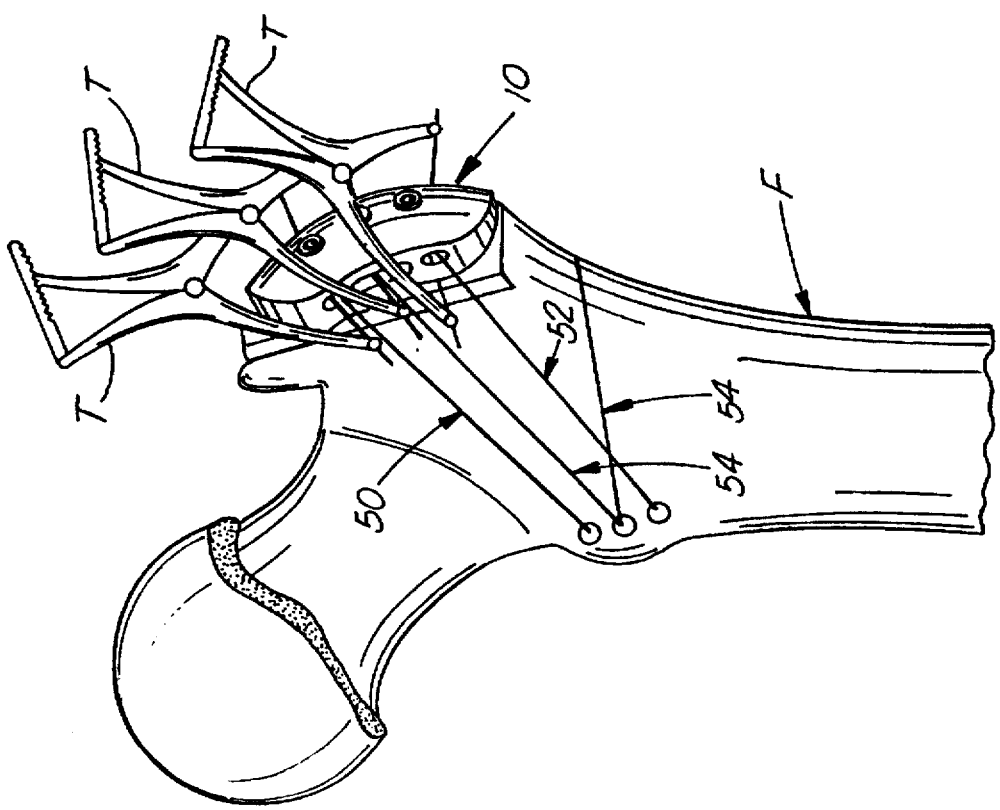
FIG. 8 is a posterior view of the femur of FIG. 2, wherein cable tensioners have been applied to tension the attachment cables and screws have been inserted into the clamp of one embodiment of the present invention.

As shown in FIG. 8, after the cables 50, 52 and 54 are threaded through the through bores 26, 34 and 18, the respective ends of the cables are grasped by cable tensioners T on the opposite side of the clamp 10 from where each was inserted. The cable tensioners T are used to apply tension to the cables 50, 52 and 54 until tension is evenly applied across the surface of the clamp 10. The preferred tension in the wire 50, 52 and 54 generally ranges from about 125 to about 200 pounds.

Figure 9:
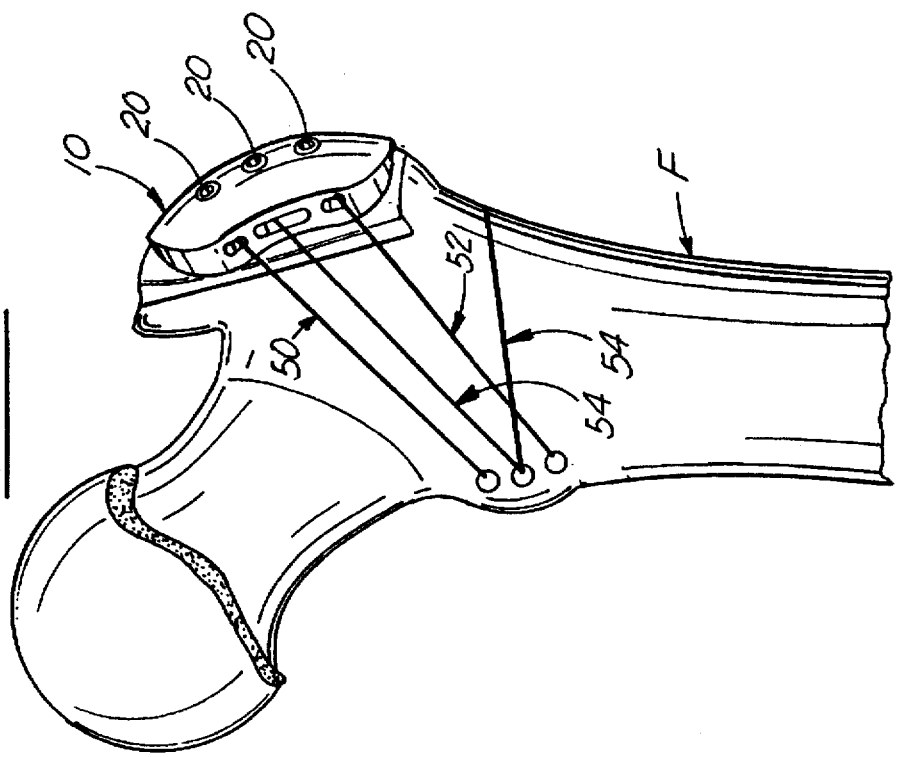
FIG. 9 is a posterior view of the femur of FIG. 2 following reattachment of the greater trochanter and illustrating the completed installation of the clamp and removed trochanter section.

Referring to FIGS. 8 and 9, assembly of the cable system is completed by fastening a clamping screw 20 into each threaded opening 38, 54 and 66 to clamp or anchor the cables 50, 52 and 54 against the inner surfaces 71 of the through bores 18, 34 and 26. The cables are positively engaged across the entire surface of the base of each of the screws 20 by controlled tightening of the screws.

As shown in FIG. 9, after the screws 20 are tightened to clamp the cables against the inner surfaces 71 of the through bores, the tensioners T are released and removed. The ends of the wires 50, 52 and 54 are then trimmed so that the ends lie within their respective through bores in clamp 10. The trimming operation is preferably performed using a guillotine type cutter (not shown) to minimize the possibility of the cable ends fraying. The clamp could also be formed with countersunk holes (not shown) so that cancellous bone screws could be used as a supplemental connection to the underlying bone for additional initial stability.

The invention is directed primarily to the use of mechanical clamping elements for clamping the cables 50, 52 and 54 in place in the through bores 26, 34 and 18. While the screws 20 are described in conjunction with the threaded openings 38, 54 and 66, other means for holding the cables in place, in the manner described, could also be used.

By using clamps, along with the clamping devices and cables as described above, a greater trochanter or other bone section can be reattached after surgery and held firmly in place during the healing process. Rotating and shifting of the clamp and reattached bone section when the patient walks or rises out of a sitting position are resisted because the cables and clamp are positioned to counteract the forces acting on the clamp.

The foregoing disclosure and description of the invention are illustrative and explanatory thereof. Upon reading this disclosure, various changes in the size, shape, and materials, as well as in the details of the illustrated construction may become apparent to one of ordinary skill in the art. These are within the scope and spirit of the invention as disclosed above and claimed below.

What is claimed is:

1. A bone section reattachment apparatus for fusing a surgically removed dome portion of the greater trochanter to the patient's femur comprising;
    a) a plate-like member having an outer convex surface and an inner concave surface that is sized and shaped to conform generally to the outer surface of the removed dome portion;
    b) the plate-like member having a peripheral surface that extends between the outer and inner surfaces, the peripheral surface including opposed anterior and posterior peripheral portions;
    c) a plurality of passageways extending transversely through the plate-like member and communicating with the opposed anterior and posterior portions of the peripheral surface of the plate-like member, each of the passageways having an inner wall surface;
    d) each of the passageways having opposed anterior and posterior openings positioned respectively on the opposed peripheral anterior and posterior portions of the peripheral surface;
    e) a plurality of generally vertical bores, each extending from the outer convex surface of the plate-like member to a passageway;
    f) a plurality of elongated cables, each having cable ends that extend respectively through the plurality of passageways, each of said passageways being sized and shaped to allow overlapping of the cable ends at the passageway so that the cable ends of a particular cable can be overlapped and secured within the passageway;
    g) a plurality of fasteners that respectively occupy the plurality of vertical bores during use, each of said fasteners forming a connection with a vertical bore that enables pressure to be applied to a pair of overlapped cable ends in a passageway;
    h) the cables being of a length that enables a surgeon to pass each cable around the patient's femur and to pass the opposed cable ends through respective opposed openings of a passageway and into the passageway a distance that allows the cable ends to be overlapped, and then held in such overlapped position by a fastener; and
    i) projecting portions extending distally from the inner concave surface of the plate-like member and being of sufficient length to extend into the removed dome portion.

2. The bone section reattachment apparatus of claim 1 wherein each of the vertical bores has a fastener and two cable ends are clamped by a fastener against the inner wall surface of a passageway during use.

3. The bone section reattachment apparatus of claim 1 wherein a plurality of the vertical bores are internally threaded.

4. The bone section reattachment apparatus of claim 3 wherein each of the fasteners is a set screw with external threads that engage an internally threaded vertical bore.

5. The bone section reattachment apparatus of claim 4 wherein each set screw has a lower end that is shaped to clamp a pair of the cable ends of a cable.

6. The bone section reattachment apparatus of claim 1 wherein at least one of the passageways has an oval shaped transverse cross section.

7. The bone section reattachment apparatus of claim 1 wherein the longitudinal axes of the passageways perpendicularly intersect a line that is curved to track generally the curvature of the concave surface of the plate-like member.

8. The bone section reattachment apparatus of claim 1 wherein there are three passageways.

9. The bone section reattachment apparatus of claim 1 wherein the passageways have longitudinal axes that are generally parallel to one another.

10. The bone section reattachment apparatus of claim 1 wherein the projecting portions are of sufficient length to extend through the removed dome portion.

11. The bone section reattachment apparatus of claim 1 wherein one of the passageways has a narrowed central section and a pair of enlarged sections at the anterior and posterior openings of the passageway.

12. The bone section reattachment apparatus of claim 1 wherein the projecting portions are a plurality of elongated spikes.

13. The bone section reattachment apparatus of claim 1 wherein the projecting portions each have a central axis and the axes of the projecting portions are parallel.

14. A bone section reattachment apparatus for fusing a surgically removed dome portion of the greater trochanter to the patient's femur comprising;
- a) a plate-like body having an outer convex surface and an inner concave surface that is sized and shaped to conform generally to the outer surface of the removed dome portion;
- b) the plate-like body having an extended peripheral surface that extends between the outer and inner surfaces, defining a spacing between the inner and outer surfaces, the plate-like body being of a solid structural material within an interior of the plate-like body that is defined by the inner and outer surfaces and the peripheral surface;
- c) a plurality of passageways extending transversely through the solid structural material of the plate-like body and communicating with opposed anterior and posterior portions of the peripheral surface of the plate-like body, each of the passageways having an inner wall surface that is spaced from both the inner and outer surfaces;
- d) each of the passageways having opposed anterior and posterior openings positioned respectively on the anterior and posterior opposed portions of the peripheral surface;
- e) a plurality of generally vertical bores extending from the outer surface of the plate-like body to at least a plurality of said passageways;
- f) a plurality of elongated cables, each having cable ends that extend respectively through the plurality of passageways, each of said passageways being sized and shaped to allow overlapping of the cable ends at the passageway so that the cable ends of a particular cable can be overlapped and secured within the passageway;
- g) a plurality of fasteners that respectively occupy the plurality of vertical bores during use, each of said fasteners forming a connection with a vertical bore that enables pressure to be applied to a pair of overlapped cable ends in a passageway;
- h) the cables being of a length that enables a surgeon to pass each cable around the patient's femur and to pass the opposed cable ends through respective opposed openings of a passageway and into the passageway a distance that allows the cable ends to be overlapped, and then held in such overlapped position by a fastener; and i) projecting portions extending distally from the inner concave surface of the plate-like body and being of sufficient length to extend into the removed dome portion.

* * * * *